(12) United States Patent
Ziran et al.

(10) Patent No.: US 8,702,705 B2
(45) Date of Patent: Apr. 22, 2014

(54) ELECTROMECHANICALLY DRIVEN EXTERNAL FIXATOR AND METHODS OF USE

(76) Inventors: Bruce H. Ziran, Boardman, OH (US); Brian S. Perala, Warren, OH (US)

(*) Notice: Subject to any disclaimer, the term of this patent is extended or adjusted under 35 U.S.C. 154(b) by 569 days.

(21) Appl. No.: 11/716,176

(22) Filed: Mar. 9, 2007

(65) Prior Publication Data

US 2007/0225704 A1     Sep. 27, 2007

Related U.S. Application Data

(60) Provisional application No. 60/785,240, filed on Mar. 23, 2006.

(51) Int. Cl.
*A61B 17/66* (2006.01)

(52) U.S. Cl.
USPC .......................................................... 606/57

(58) Field of Classification Search
USPC .................................................... 606/53–59
See application file for complete search history.

(56) References Cited

U.S. PATENT DOCUMENTS

| | | | | |
|---|---|---|---|---|
| 4,889,111 A * | 12/1989 | Ben-Dov | | 606/56 |
| 5,108,394 A * | 4/1992 | Kurokawa et al. | | 606/59 |
| 5,180,380 A * | 1/1993 | Pursley et al. | | 606/54 |
| 5,207,676 A * | 5/1993 | Canadell et al. | | 606/54 |
| 5,314,426 A * | 5/1994 | Pohl et al. | | 606/58 |
| 5,454,810 A * | 10/1995 | Pohl et al. | | 606/59 |
| 5,601,551 A * | 2/1997 | Taylor et al. | | 606/54 |
| 5,688,271 A * | 11/1997 | Faccioli et al. | | 606/54 |
| 5,971,984 A * | 10/1999 | Taylor et al. | | 606/54 |
| 6,017,341 A * | 1/2000 | Windhagen et al. | | 606/56 |
| 6,113,599 A * | 9/2000 | Landsberger | | 606/60 |
| 6,428,540 B1 * | 8/2002 | Claes et al. | | 606/53 |
| 6,701,174 B1 * | 3/2004 | Krause et al. | | 600/407 |
| 7,881,771 B2 * | 2/2011 | Koo et al. | | 600/426 |
| 2002/0010465 A1 * | 1/2002 | Koo et al. | | 606/57 |
| 2004/0059331 A1 * | 3/2004 | Mullaney | | 606/59 |
| 2004/0073211 A1 * | 4/2004 | Austin et al. | | 606/54 |
| 2004/0097922 A1 * | 5/2004 | Mullaney | | 606/53 |

* cited by examiner

*Primary Examiner* — Jerry Cumberledge
(74) *Attorney, Agent, or Firm* — Gary P. Topolosky (57) ABSTRACT

A device for electromechanically and/or electro-pneumatically positioning a fractured bone having a first clamping unit adapted for attachment to the bone by at least one first bone fastener, a second clamping unit adapted for attachment to the bone by at least one second bone fastener, and at least one of: (i) a translation component operatively driven by a translational driver for relative translational movement of one clamping unit with respect to the other along a translational axis; (ii) an angulation component operatively driven by an angulational driver for relative angulational movement of one clamping unit with respect to the other along an articulation axis; and (iii) a rotational component operatively driven by a rotational driver for relative rotational movement of one clamping unit with respect to the other along a rotational axis.

17 Claims, 12 Drawing Sheets

ELECTROMECHANICALLY DRIVEN EXTERNAL FIXATOR AND METHODS OF USE

CROSS-REFERENCE TO RELATED APPLICATIONS

This application claims the benefit of priority to U.S. Provisional Application Ser. No. 60/785,240, filed on Mar. 23, 2006 and fully incorporated by reference herein.

FIELD OF THE INVENTION

The present invention relates to surgical orthopedic instrumentation and to the external fixation of bone fractures. More particularly, this invention relates to electromechanical means for making automatic, multiple axis, multi-dimensional adjustments to bone fractures.

BACKGROUND OF THE INVENTION

External fixators have been in use for over a century. The first recorded use was by Wilhelm Wutzer (1789-1863) who used pins and an interconnecting rod in a clamping system to repair badly broken bones. Parkhill (1897) and Lambotte (1900) used unilateral devices with four pins and a bar/clamp system. By the 1960's, Vidal and Hoffman popularized using external fixators for open fractures and infected pseudarthroses. The problems expressed with fixation in the late $20^{th}$ century, however, were mostly due to lack of understanding about its basic principles of application and healing. Therefore, external fixator (or "EF") use was relegated to the most severe of injuries wherein infections, pin problems, non-unions, and mal-unions were all too common.

Since the 1950's, Ilizarov took developed principles and expounded on the ring and wire style of then, external fixation devices with excellent success. It was not until the late 1980's and early 1990's, when there was better communication with the Western world (after the fall of the former Soviet Union), that the methods of Ilizarov and thus, external fixation, were more easily demonstrated to the West. External fixation has now become so refined that it is now a potent tool in the management of orthopedic fractures, with or without complicated conditions. Currently, in the United States, external fixators have two widespread uses: in a damage control orthopedics (DCO) frame which is meant to be temporary, and in a treatment frame intended for a longer term, definitive treatment.

When external fixation is used for deformity or limb salvage, the device may require certain abilities for successful treatment. It should be able to lengthen and shorten as well as correct angular or rotational deformities. The original wire fixator design of Ilizarov utilized rings and tensioned fine wires that were connected together into an assembly with threaded rods. Use of hinges, and other accessories allowed the device to correct numerous conditions. These included all of the pre-requisites of lengthening-shortening, angular and rotational deformities. However, due to its completely manual nature, it required a significant amount of expertise and management. Subsequently, many surgeons in the United States did not employ the device routinely.

Some time later, the Taylor Spatial frame was developed using the science of the Stewart Platform, a device used to develop flight simulators. It allowed for a programmable multi-axis motion. The Taylor Spatial Frame utilized the hexapod mechanism of the Stewart Platform. It is placed on a limb segment with a ring above and below the deformity. The relative position of the rings to each other is readily known by the position of each of the six struts of the hexapod construct. The position of the construct to one limb segment is also known by use of radiographic measurements. Thus, by virtue of the known relationship of one limb segment to one ring, and the rings to themselves, the opposing limb segment's position is known since it is technically part of the same rigid body of the second ring.

Using a web based software program, the parameters can be used to create a corrective prescription that results in a relative motion between each ring, and therefore, each limb segment. A radiographic measurement of the resulting correction is performed and if needed, another iteration of the program for correction is performed, to result in a residual correction. Each corrective iteration is described by a prescription that outlines the adjustments in each hexapod strut. These maneuvers are performed manually by the surgeon or patient. Currently, the Taylor Spatial Frame is the only device available that provides a semi-manual three dimensional correction.

Other available fixators that can provide three-dimensional adjustments are mono-planar and utilize a series of hinges. These are not progressively adjustable like the struts of the Taylor Frame, and there is no web based software program that can be used. Some efforts at providing a uni-axial correction, e.g., axial motion such as a lengthener, have been developed. Still, these devices require experience for correct placement and are manually driven.

The device in the present patent utilizes the characteristics of both the mono-planar fixators as well as kinematic programming to effect a three dimensional correction of two limb segments. Instead of a ring-hexapod methodology, however, this fixator utilizes a mono-planar or series of mono-planar segments that have one or more electromechanical elements that can effect motion automatically. The elements are positioned in a prescribed arrangement around the limb, and its relationship to the limb segment is established. Each electromechanical element has a known position relative to others and to the limb. Using known 3-D kinematic calculations, the corrective formula can be determined, and signals to each motorized element determine the rate and amount of correction.

The said elements can have the ability to communicate using standard wireless technology, and can retain a history of position, force, and rate. Such electronic and recording capability can also be used to establish the compliance of the patient and working reliability of the device. The fixator described in this report can be attached to any fixator element in each limb segment. The ability to attach to a ring, a clamp, or other pin-bar construct allows its use with a variety of other products, and it is subsequently functioning as a connecting rod.

Several studies have tackled the different healing patterns of fractures in various external fixators. These studies have all attempted to measure fracture callous stiffness and strain during healing for outlining "how" healing occurs. The basic principle is that of progressive load transfer. If a bone fracture is going to heal, ensuring a proper load transfer to develop callous is necessary. The first stage of external fixation attempts to achieve a rigid and still construct for allowing induction of the healing process as well as letting the adjacent soft tissues time to "recover". Once that biologic potential is realized, the EF frame progressively "de-stiffens" to transfer more and more load to the newly developing callous. If the construct is made too flexible, too early, the resultant strain may exceed the limits of that callous. And if there is not insufficient EF load transfer, some bone resorption and disuse osteopenia may result, both of which are undesirable. EF de-stiffening can be performed by removing bars, adjusting the location of bars, or removing certain pin/wire components.

With ring EF designs, the load transfer is usually a repetitive stimulus that occurs with increasing functional activity. As healing progresses, wires and half pins get removed and/or support struts loosened. Finally, some of the intervening struts can be removed altogether, leaving ring/wire/pin constructs with the patient having a trial weight bearing. If there is clinical pain, the struts get reapplied with the presumption that healing is not yet complete.

SUMMARY OF THE INVENTION

The present invention provides a device for electromechanically positioning a fractured bone comprises a first clamping unit adapted for attachment to the bone by at least one first bone fastener; a second clamping unit adapted for attachment to the bone by at least one second bone fastener; and at least one of: (i) a first translation component operatively driven by a translational electromechanical driver for relative translational movement of one clamping unit with respect to the other along a first translational axis; (ii) a first angulation component operatively driven by an angulational electromechanical driver for relative angulational movement of one clamping unit with respect to the other along a first articulation axis; and (iii) a first rotational component operatively driven by a rotational electromechanical driver for relative rotational movement of one clamping unit with respect to the other along a first rotational axis. The combined utility of the device would allow an automated motion in at least one axis.

BRIEF DESCRIPTION OF THE DRAWINGS

Still other advantages of the present invention will become apparent to those skilled in the art after reviewing the detailed description that follows made with reference to accompanying drawings in which:

FIG. 1b is a close up schematic for the B-B circled region of FIG. 1a;

DETAILED DESCRIPTION OF PREFERRED EMBODIMENTS

As described herein below, the term "positioning" is also meant to expressly address the need for subsequent bone "re-positioning" as well. And, while repeated references are made to uses to repair fractured bone by the methods and apparatus of this invention, it should be equally understood to address beyond "broken bone" repairs, the possibilities for both mal-union and non-union, or as a slow bone correcting device. (i.e. the purposeful correction of misaligned or non-healed bones). The deformity of the bone would be an independent variable, and its correction would be such to place it in an anatomic or mechanical axis. The gradual correction would occur in multiple planes and be driven by the coordinated movements of each electromechanical component. In addition, using the same electromechanical elements, the external fixator can be used for intentional compression to stimulate partially healed bone. Furthermore, in the event of missing sections of bone, the device can be used to perform bone transport. In this configuration, one or more of the bone fixation units would be powered to move relative to others, so as to result in a relative transport of one bone segment with another. It would do so in a prescribed fashion so as to result in "bone regeneration". The use of modular segments give the fixator attached thereto greater options for application. It can easily be assembled to specific, sometimes even awkward configurations, positioning its various hinges on where the patient most needs that degree of movement.

In some embodiments depicted, the hinges of one part of the fixator are knowingly passive. Nevertheless, they can be made to accept motorized drives like those schematically depicted in accompanying FIGS. 1a and 1b. With such a configuration, the EF device may get calibrated for an initial positioning thereby generating an initial, or "start up" position. The initial position will serve as a baseline after which CPU programming, either full time on-board, or off-board, can be used for calculating the patient's next corrective steps and ex-fix movements relative to same. Finally, with a series of force gauges or other monitoring means, the stiffness of intervening bone can be calculated using standard mechanical and physics formulas. By knowing the distance of the force transducer from the bone segment in question, and knowing the material and mechanical properties of the fixator and pin device, the amount of force generated with load can be used to calculate the stiffness or modulus of the intervening bone segment. This modulus or stiffness of the "callus" can provide knowledge of the consolidation of the intervening bone segment. This information can be used to determine bone healing, since as the bone heals and the callus matures, it will stiffen and accept more load, and thus share with load transfer. When this occurs, the force sensed by the transduction elements will decrease. Other methods using displacement have been used and described by Burny and others. This use of force is a simple substitution where in stiffness is substituted for displacement during the determination of healing.

The changes in such "fracture stiffness" or modulus can be periodically detected . . . and reported out, for assessing when the proper degree of bone healing has transpired. The measurements can be recorded and even transmitted to a device in a wireless fashion and can be transmitted to office of the surgeon for monitoring. With "smart" chips, USB's and other computer-based interfaces, the load cells for this invention can conceivably take healing "information" in while also delivering information out for subsequent medical interpretation. These same devices can further be programmed to automatically correct based on a prescription determined by the deformity and surgeon.

Since the external fixator device is primarily functioning as a connecting device between different fixator components, it could potentially be used on any number of different commercially available devices. Thus, it is not restricted to use with only one external fixator design. And while there are numerous references to various motor drive mechanisms herein, it is understood that such components, or sub-components, can be driven by commercially available micro-motors with gear assemblies, or with known or subsequently developed, electro-pneumatic drive devices, i.e., the type used to drive pneumatic cylinders and the like.

Figure 1A:
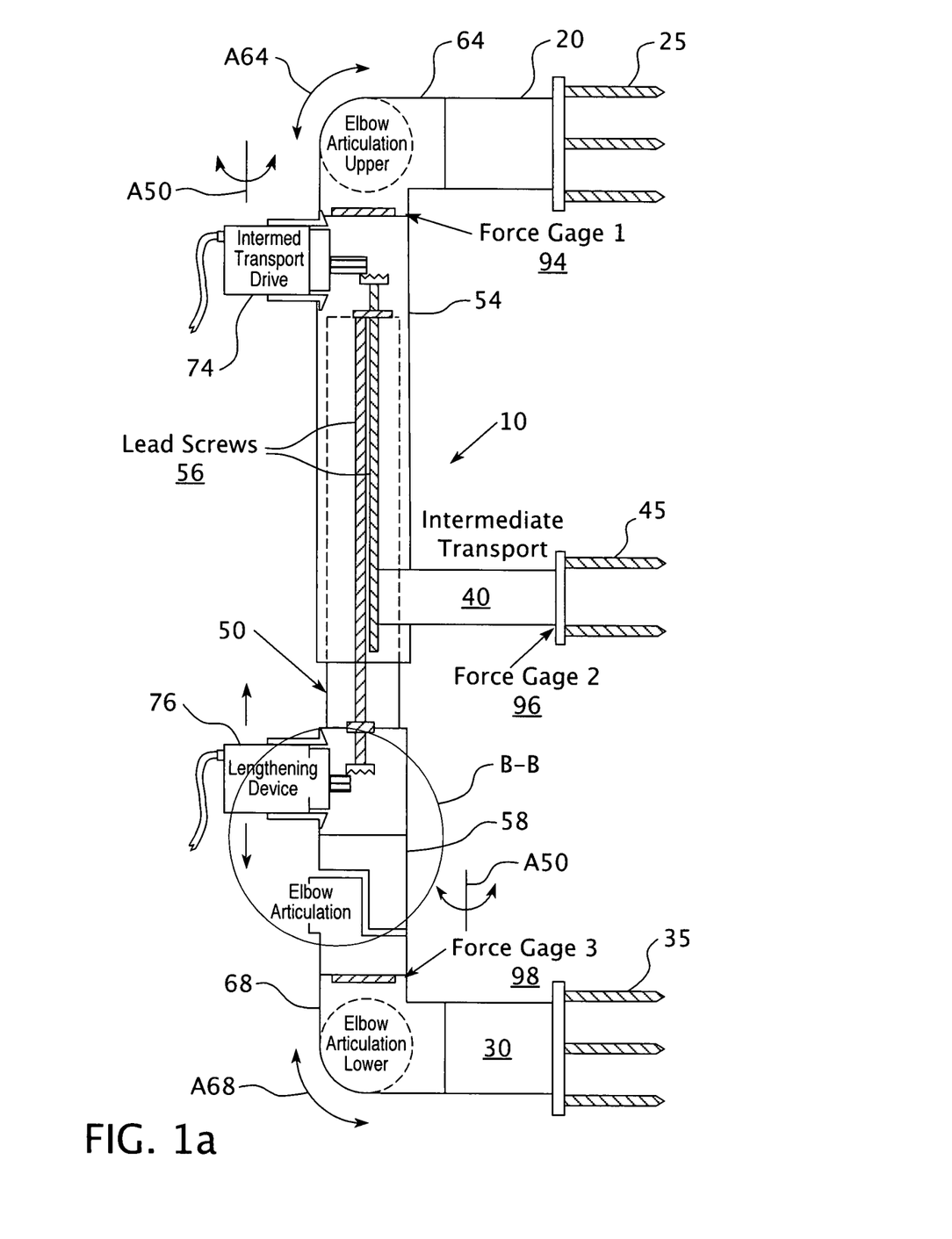
FIG. 1a is a left side (femur) schematic showing a bone positioning device according to a first preferred embodiment of the invention.
Figure 1B:
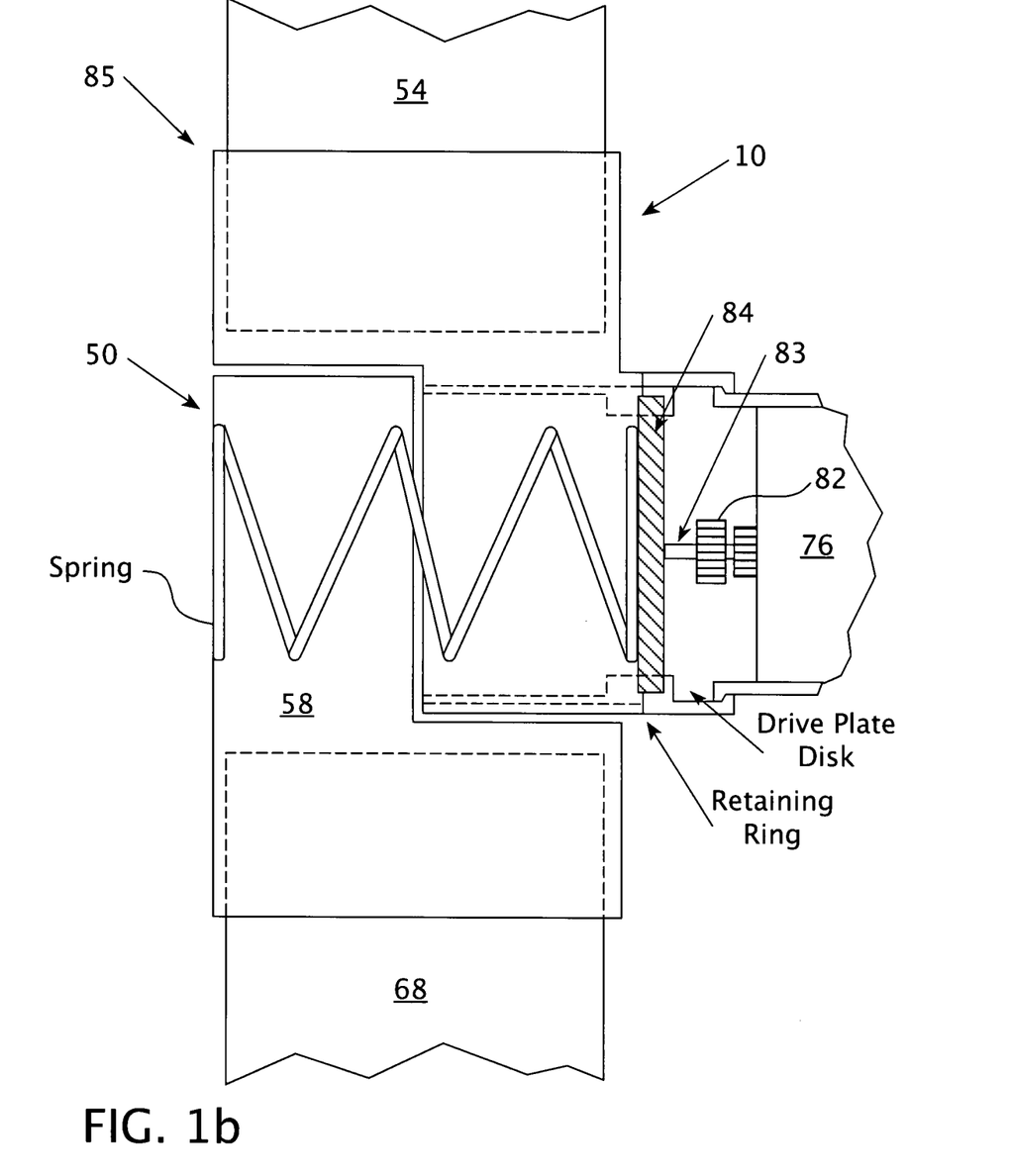
Figure 2:
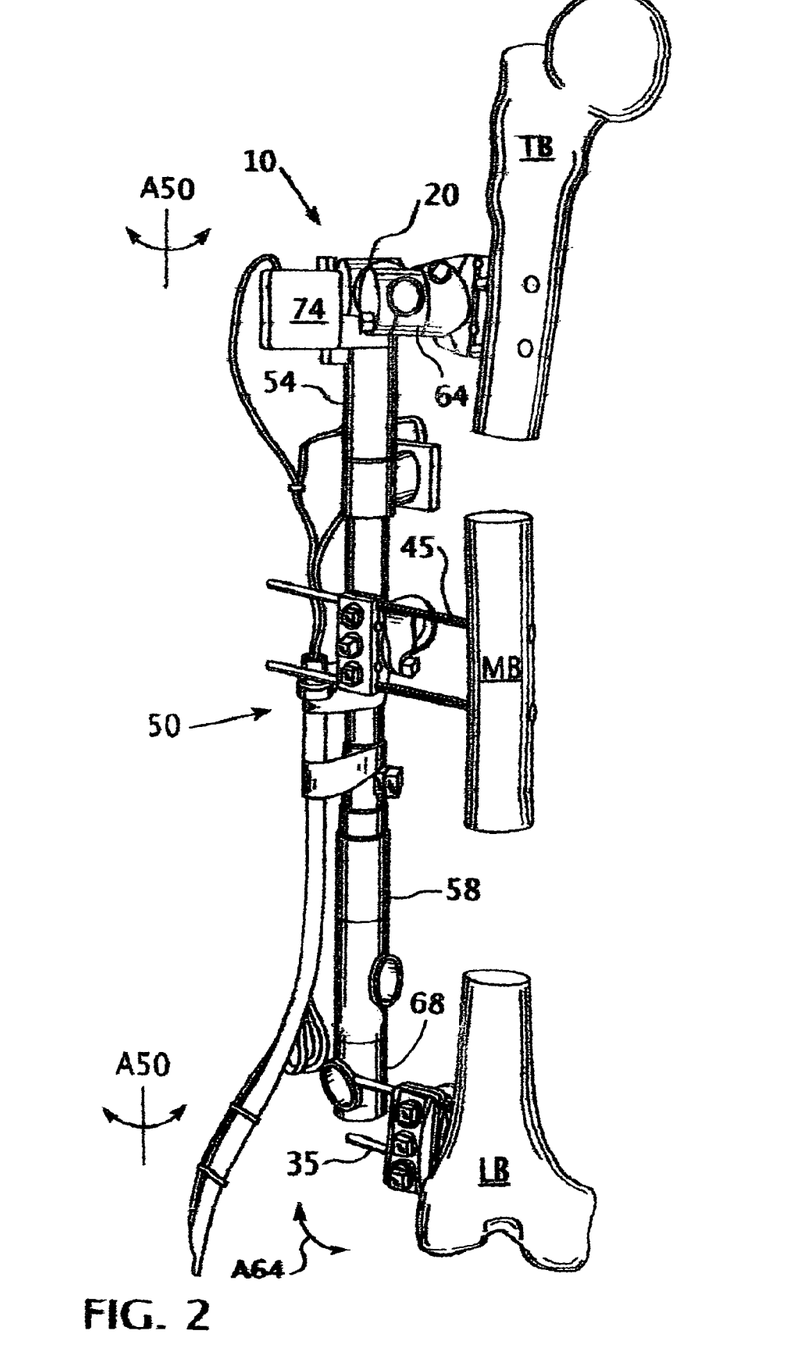
FIG. 2 is a left side (femur) posterio-medial schematic view of a bone positioning device according to a first preferred embodiment of the invention.
Figure 3:
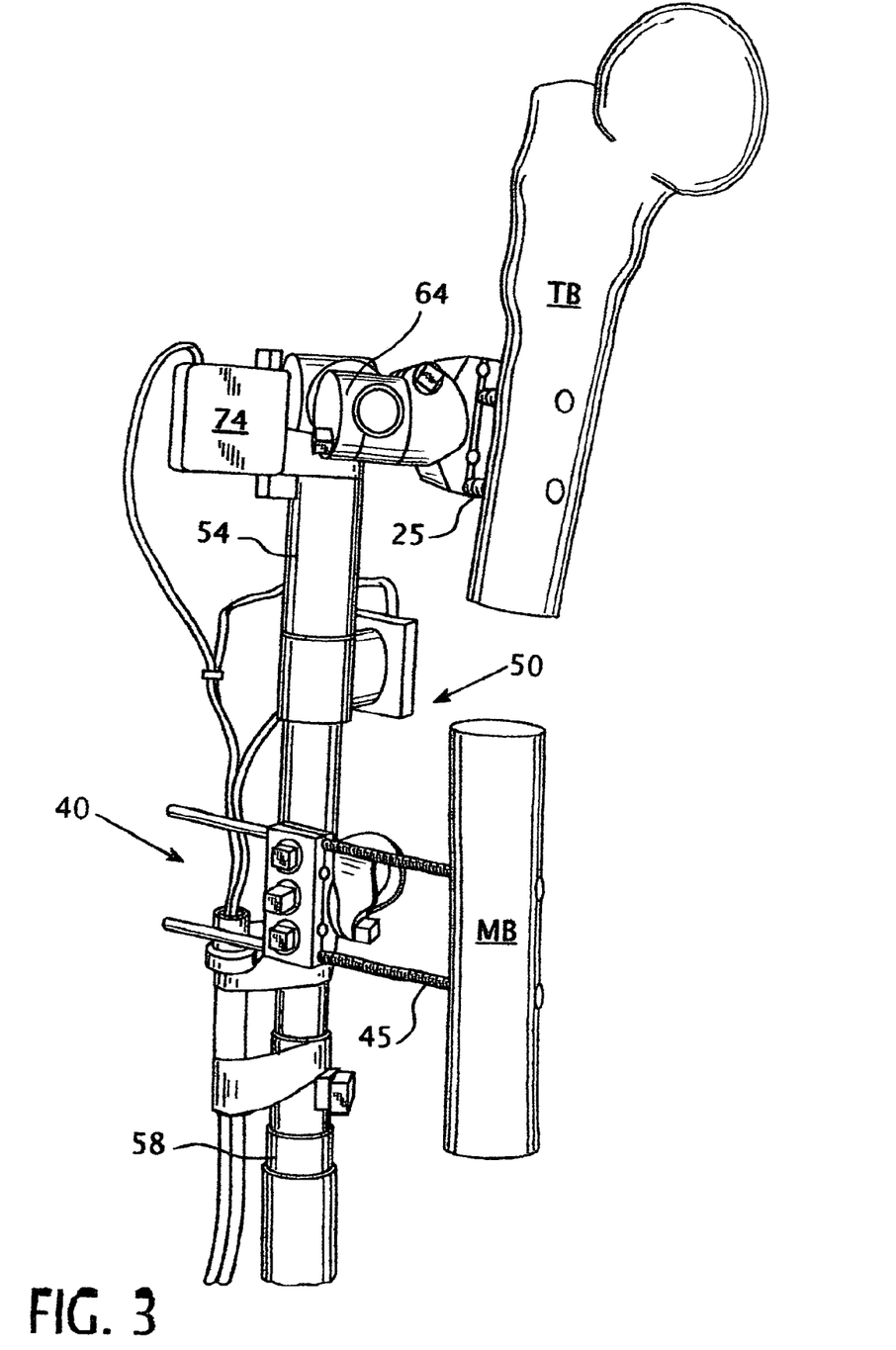
FIG. 3 is a left side (femur) posterio-medial schematic view focusing on the upper half of the device of FIG. 2.
Figure 4:
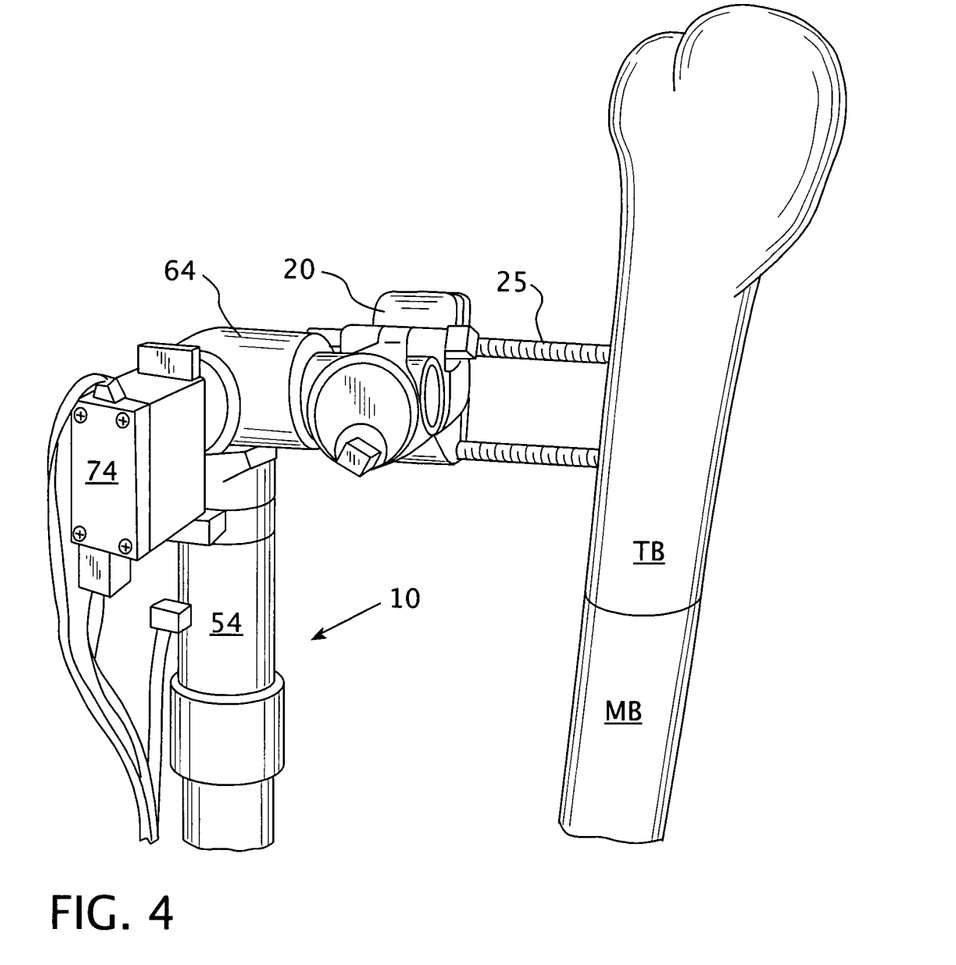
FIG. 4 is a closeup left side (femur) posterio-medial schematic view of a first operatively driven component and electromechanical driver for the proximal top two-thirds of the device of FIG. 2.
Figure 5:
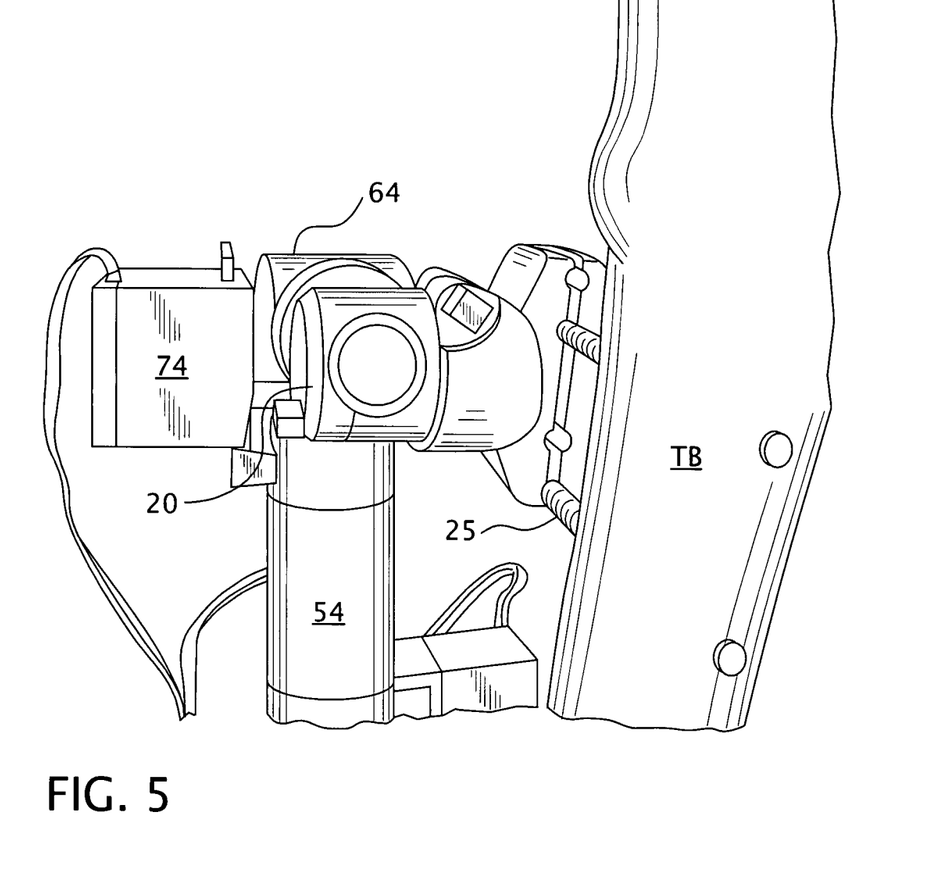
FIG. 5 is a closeup left side (femur) posterio-lateral schematic view of the first component and driver of FIG. 4 after it has been rotated clockwise about 30 degrees.
Figure 6:
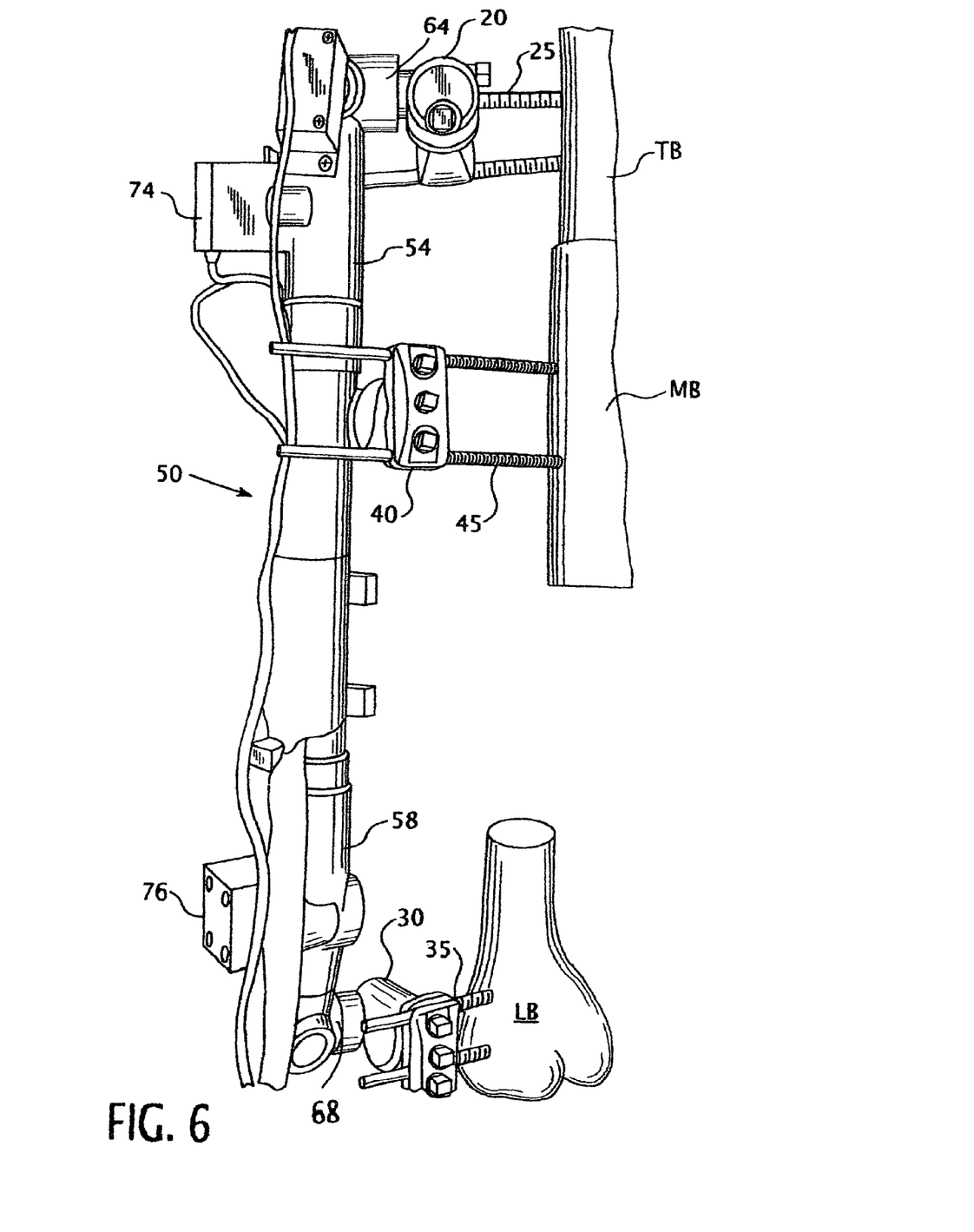
FIG. 6 is a left side (femur) posterio-medial perspective schematic focusing on the middle mechanicals for the device of FIG. 2.
Figure 7:
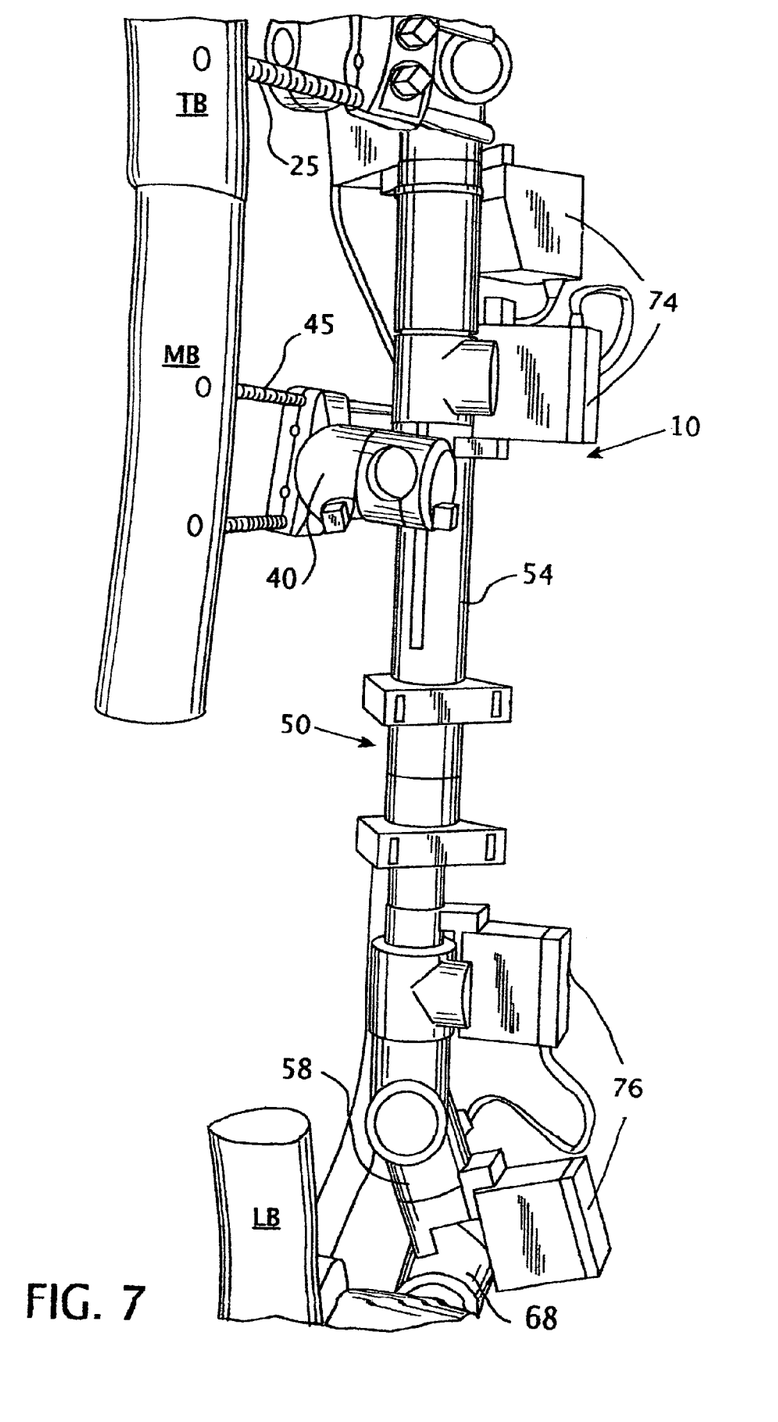
FIG. 7 is an anterior-lateral, perspective schematic of the FIG. 6 middle mechanicals.
Figure 8:
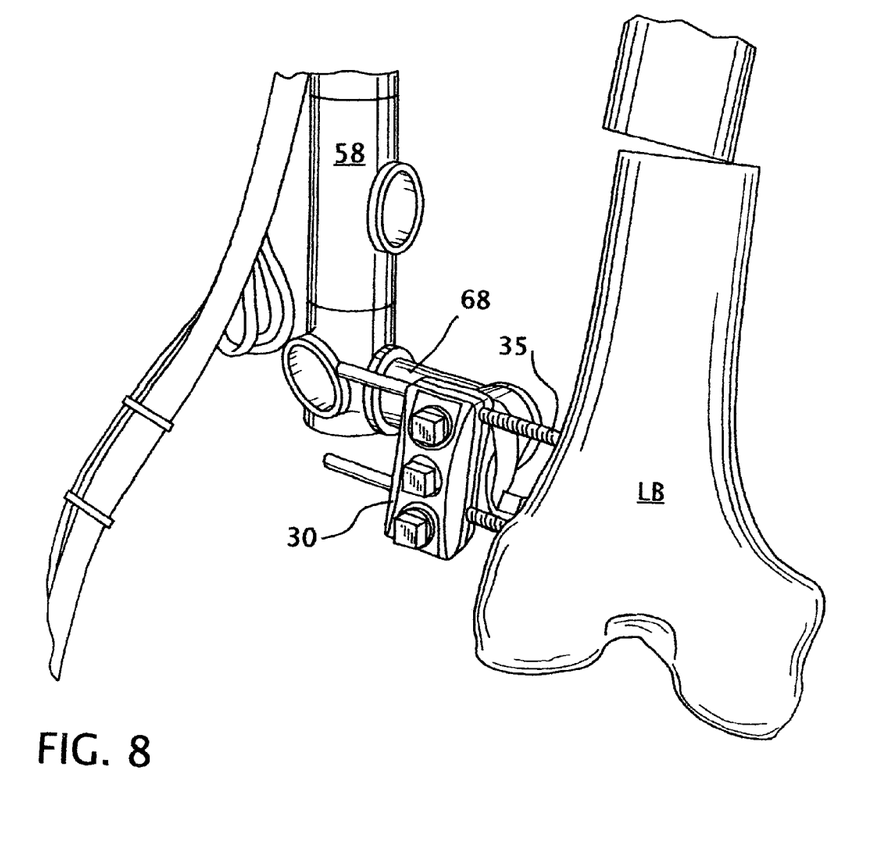
FIG. 8 is a left side (femur) posterio-medial schematic view focusing on a distal, lower one third of the device of FIG. 2.
Figure 9:
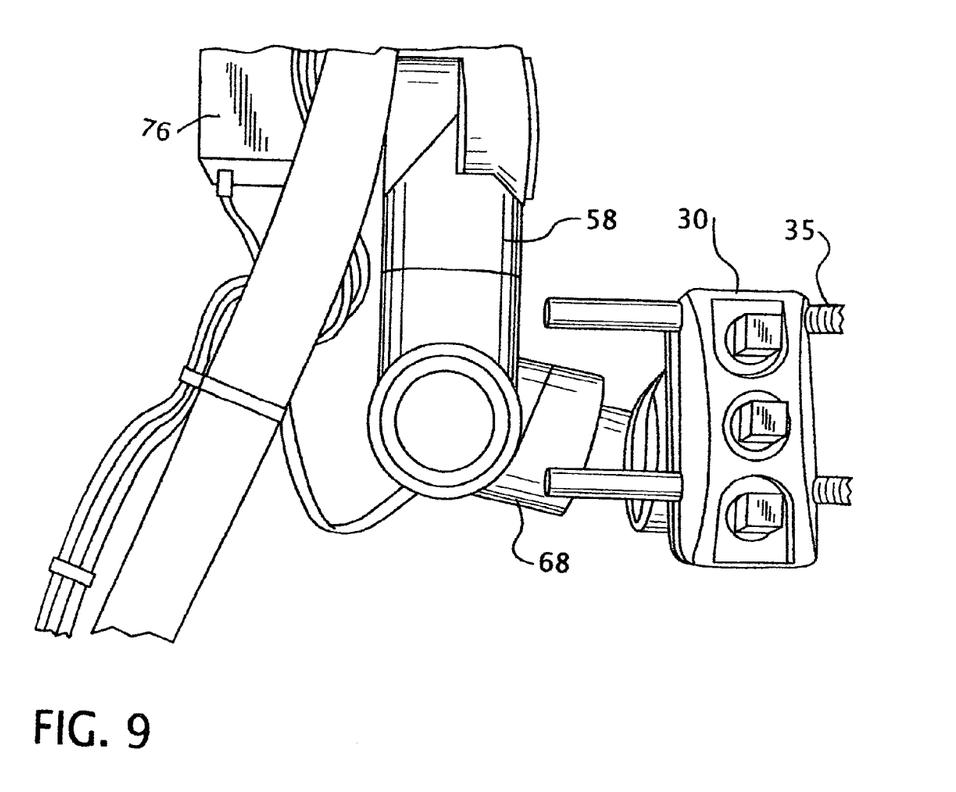
FIG. 9 is a closeup right side schematic view of a first operatively driven component and electromechanical driver for the lower half of the device of FIG. 2.
Figure 10:
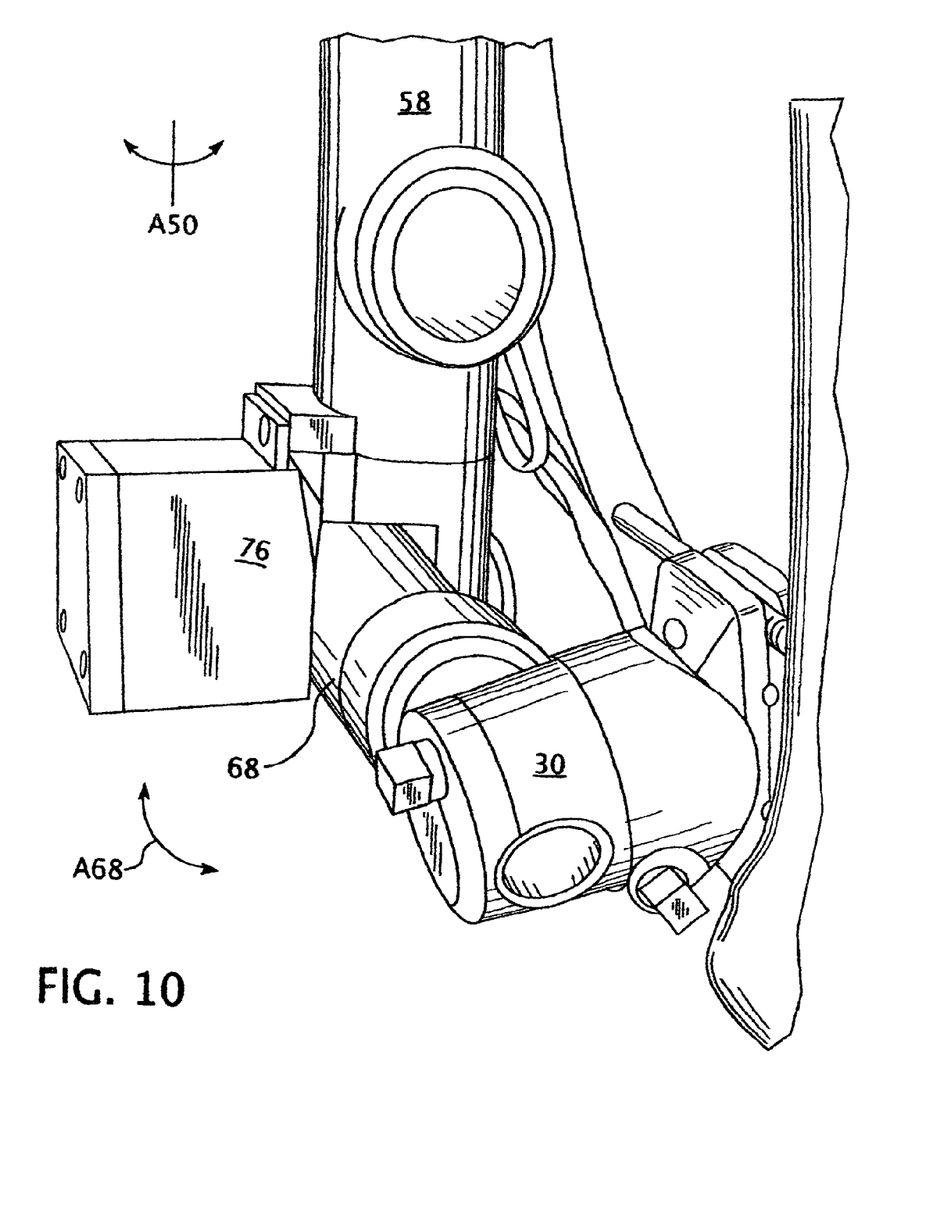
FIG. 10 is an anterio-medial, perspective schematic of the FIG. 9 lower device component and driver.
Figure 11:
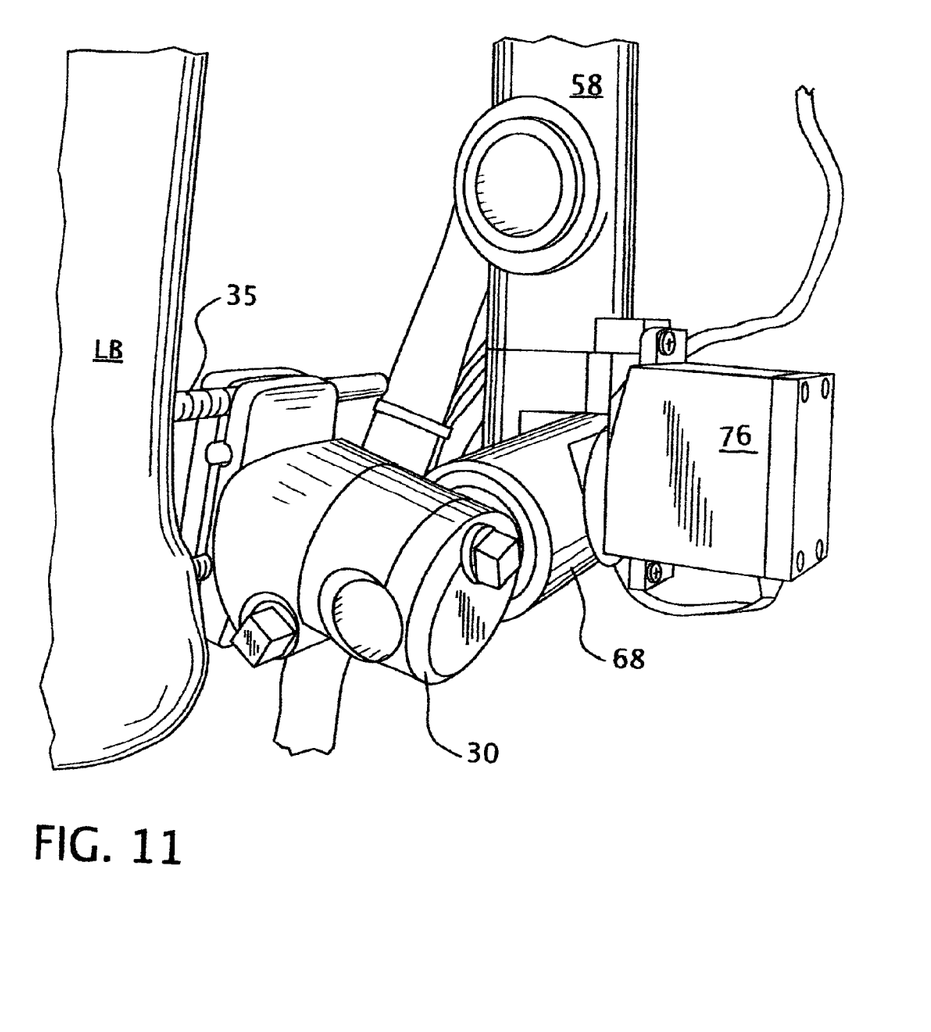
FIG. 11 is a closeup reverse angle schematic view of the distal, lower one third of the FIG. 9 device component and driver after it has been rotated clockwise about 180 degrees.

Referring now to the FIGS., especially the schematic representation of one preferred embodiment at FIG. 1a (and its close up view FIG. 1b taken from an enlargement of area B-B in FIG. 1a), there is generally shown the device 10 for electromechanically positioning a fractured bone. To better illustrate a fractured bone, in some of the accompanying photographs of this preferred embodiment, the bone connected to same is divided as a top bone TB, middle bone MB, and lower bone LB. Adjacent top bone TB, there is situated a first clamping unit 20 that is meant to attach to bone TB with a plurality of known fixator fasteners, in this case bone screws 25.

Device 10 further includes a second clamping unit 30 adapted for attaching to a lower bone LB by its own set of bone screws 35. More preferably, and for better illustrating use of this device for joining multiple bone fragments together, there is shown yet a third, more intermediate clamping unit 40 that attaches to middle bone MB via its own set of bone screws 45.

The three main clamping units of device 10 all interconnect along mainframe 50. As shown, however, mainframe 50 includes an upper portion 54 and lower portion 58. Internal to that mainframe, as best seen in partial cutaway at FIGS. 1a and 1b, there is a series of lead screws 56. By the relative, in this case electromechanical, positioning of lead screws 56, the overall relative length of mainframe 50 can increase or decrease, as needed for external fixation purposes.

At each end to mainframe 50 of device 10, there are positioned elbow articulations. At the top of upper portion 54, upper elbow articulation 64 can be found for rotating on a first axis shown by articulation arrow A64. Similarly, towards the base of mainframe 50, there is a corresponding lower elbow articulation 68 whose direction of rotation is generally shown by articulation arrow A68. The movement of these elbows provides a certain "hinge-like" quality to the relative movement of device 10 with the various bone parts to which they are connected. They account for the relative angulational movement of device 10.

Because of the manner in which elbow articulations 64 and 68 pivotally mount to the upper and lowermost tips of mainframe 50, these same elbows may be further rotated (left to right, or vice versa) about an axis that runs substantially parallel to the overall length/direction of mainframe 50. Those directions of rotational movement are marked by axial arrows A50 (both upper and lower).

For assisting with the electromechanical translation, angulation and/or rotation of device 10 about upper bone, middle bone and lower bone, there are shown an upper transport drive 74 and a more intermediate, longitudinal or lengthening drive 76. As better seen by the closeup view at FIG. 1b, the general connection means for such drives include a turning gear 82, a disengagement pin 83 to a friction plate 84 behind which a spring brake 85 is pushing away from an interior wall of device 10. Though not shown, one or more of these drives can be supplemented with and/or superseded by wormgears and/or other temporary lockout mechanisms.

In one embodiment of the invention, device 10 remains affixed to the patient's bone and can be connected, disconnected and reconnected to drives 74 and 76 for making periodic adjustments. Depending on the materials selected for mainframe 50 and the various bone connectors, as well as whether the drive units remain "on board" for near full time healing management, the device itself has the potential to be rendered MRI compatible.

To better serve the preferred functions of monitoring the healing of bone with an electromechanically driven device 10, there are a series of force gauges positioned about the mainframe 50. Preferably, an upper force gauge 94, intermediate gauge 96 and lower force gauge 98 are commonly wired for providing a feedback signal for when measurable stress and/or strain reductions have occurred, such changes from a preset norm being indicative of the degree of bone callous formed and from which subsequent movements of the fixator can be precisely planned. One such force gauge sensor is a Flexiforce pressure sensor as made and sold by Parallax, though it to be understood that any one or more known, or subsequently conceived, force sensors can be substituted for same.

With the aforementioned device and its preferred combinations of motors, breaks, gears, and/or lockouts, it is conceivable to automatically move one or more connection points to a patient's anatomy slowly and smoothly between in a plurality of axes. In other words, this device allows for a better transition from starting points ABC to end points XYZ without having to go in just one direction, i.e., all along a vertical, from A to X, then along the horizontal, from B to Y, etc. But instead, through a more "flowing" synchronicity of axial movements, this device can transfer the patient gradually, and less painfully, from beginning A to desired end point Z.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A progressively adjustable device adapted for electromechanically positioning a bone, said device having a tubular-shaped mainframe with elbow articulations at each end, each elbow articulation having means for electromechanically rotating about an axis to provide relative angulational movement of the device to the bone, the axis being transverse to a longitudinal axis of the tubular-shaped mainframe, said device further comprising:
a first clamping unit adapted for attachment to the bone by at least one first bone fastener;
a second clamping unit adapted for attachment to the bone by at least one second bone fastener;

a translation component operatively driven by a first electromechanical drive for relative translational movement of one clamping unit with respect to the other, either independent or dependent of one another, along a translational axis; and at least one force gauge with an output that is a variable of programmability, the force gauge being located proximate either the first or the second clamping unit.

2. The electromechanical positioning device of claim 1 which can be disconnected from and reconnected to the bone.

3. The electromechanical positioning device of claim 1, which is adapted for positioning the bone in more than two directions.

4. The electromechanical positioning device of claim 1, wherein the first and second electromechanical drives are independently programmable.

5. The electromechanical positioning device of claim 1 which is further able to provide intentional compression for stimulating bone growth.

6. An automated device adapted for electromechanically positioning a bone, said device comprising a tubular mainframe with articulating elbows at opposing ends and:

a first clamping unit adapted for attachment to the bone by at least one first bone fastener;

a second clamping unit adapted for attachment to the bone by at least one second bone fastener;

a first angulation component operatively driven by a first electromechanical drive for relative angulational movement of one clamping unit at a first articulating elbow with respect to the other articulating elbow about an angulational axis, the angulational axis being transverse to a longitudinal axis of the tubular mainframe;

a rotational component operatively driven by a second electromechanical drive for relative rotational movement of one clamping unit with respect to the other about a rotational axis, the rotational axis being transverse to the angulation axis; and at least one force gauge with an output that is a variable of programmability, the force gauge being located proximate either the first or the second clamping units.

7. The automated electromechanical positioning device of claim 6 which further comprises a rotational component operatively driven by a second electromechanical drive for relative rotational movement of the clamping unit at the other articulating elbow with respect to the first articulating elbow.

8. The automated electromechanical positioning device of claim 7, wherein the first and second electromechanical drives are independently programmable.

9. The automated electromechanical positioning device of claim 6 which can be disconnected from and reconnected to the bone.

10. The automated electromechanical positioning device of claim 6, which is adapted for positioning the bone in more than two directions.

11. The automated electromechanical positioning device of claim 6 which is further able to provide intentional compression for stimulating bone growth.

12. A device adapted for providing without any ring-hexapod structure three-dimensional adjustment to a bone, said device being generally tubular with articulating elbows at each end, the articulating elbows articulating along respective angulation axes transverse to a longitudinal axis of the device, and further comprising:

a first clamping unit adapted for attachment to the bone by at least one first bone fastener;

a second clamping unit adapted for attachment to the bone by at least one second bone fastener;

a first rotational component operatively driven by a first electromechanical or electropneumatic drive for relative rotational movement of the first clamping unit at a first articulating elbow with respect to the second clamping unit about a rotational axis, the rotational axis being transverse to the angulation axes;

a second rotational component operatively driven by a second electromechanical or electropneumatic drive for relative rotational movement of the second clamping unit at a second articulating elbow with respect to the first clamping unit about a second rotational axis, the second rotational axis being transverse to the angulation axes; and at least one force gauge with an output that is a variable of programmability, the force gauge being located proximate either the first clamping unit or the second clamping unit.

13. The device of claim 12 which further comprises a translation component operatively driven by a third electromechanical or electropneumatic drive for relative translational movement of a third clamping unit intermediate the first and second clamping units.

14. The device of claim 13, wherein the first and second drives are independently programmable.

15. The device of claim 12, which is adapted for positioning the bone in more than two directions.

16. The device of claim 12 which is further able to provide intentional compression for stimulating bone growth.

17. A generally tubular-shaped device with articulated elbows at each end, said device adapted for running substantially parallel to a bone to electromechanically or electropneumatically position same, said device comprising:

a first clamping unit adapted for attachment to the bone by at least one first bone fastener;

a second clamping unit adapted for attachment to the bone by at least one second bone fastener;

a translation component operatively driven by a translational electromechanical or electropneumatic drive for relative translational movement of one clamping unit with respect to the other along a translational axis;

an angulation component operatively driven by an angulational electromechanical or electropneumatic drive for relative angulational movement of one clamping unit with respect to the other about an articulation axis, the articulation axis being transverse to a longitudinal axis of the generally tubular-shaped device;

a rotational component operatively driven by a rotational electromechanical or electropneumatic drive for relative rotational movement of one clamping unit with respect to the other about a rotational axis, the rotational axis being transverse to the articulation axis;

at least one of the components being modular, said device being capable of assembly in at least one configuration or a number of different configurations suitable for each particular application and further being able to provide intentional compression for stimulating bone growth; and at least one force gauge with an output that is a variable of programmability, the at least one force gauge being located proximate either the first clamping unit or the second clamping unit.

* * * * *